(12) United States Patent
Gandhi et al.

(10) Patent No.: US 12,325,847 B2
(45) Date of Patent: Jun. 10, 2025

(54) METHOD AND APPARATUS FOR FABRICATING HIGH ASPECT RATIO STRUCTURES

(71) Applicant: Indian Institute of Technology Bombay, Mumbai (IN)

(72) Inventors: Prasanna Subhash Gandhi, Mumbai (IN); Makrand Ashok Rakshe, Satara (IN); Tanveer ul Islam, Banihal (IN)

(73) Assignee: INDIAN INSTITUTE OF TECHNOLOGY BOMBAY, Mumbai (IN)

( * ) Notice: Subject to any disclaimer, the term of this patent is extended or adjusted under 35 U.S.C. 154(b) by 98 days.

(21) Appl. No.: 17/276,104

(22) PCT Filed: Sep. 16, 2020

(86) PCT No.: PCT/IN2020/050794
§ 371 (c)(1),
(2) Date: Mar. 12, 2021

(87) PCT Pub. No.: WO2022/034597
PCT Pub. Date: Feb. 17, 2022

(65) Prior Publication Data
US 2023/0183628 A1    Jun. 15, 2023

(51) Int. Cl.
B29C 43/00    (2006.01)
C12M 1/00    (2006.01)
C12M 1/12    (2006.01)

(52) U.S. Cl.
CPC ............ *C12M 25/06* (2013.01); *C12M 23/20* (2013.01); *B29C 43/00* (2013.01)

(58) Field of Classification Search
CPC ......................... B29C 43/00; B81C 1/00126
See application file for complete search history.

(56) References Cited

U.S. PATENT DOCUMENTS

2005/0011873 A1*   1/2005   Withford ............ B23K 26/066
                                           219/121.69

FOREIGN PATENT DOCUMENTS

WO   WO-2017094021 A1 *   6/2017   ......... B81C 1/00126

OTHER PUBLICATIONS

Islam, Viscous Fingering in Multiport Hele Shaw Cell for Controlled Shaping of Fluids, Scientific Reports vol. 7, 2017 (Year: 2017).*

* cited by examiner

*Primary Examiner* — Virak Nguon

(57) ABSTRACT

Embodiments herein disclose a method for fabricating high aspect ratio structures. The method includes depositing a predefined quantity of a viscoelastic fluid on a top surface of a bottom cell plate and compressing the viscoelastic fluid deposited on the top surface of the bottom cell plate using a bottom surface of a top cell plate. The viscoelastic fluid is a blend of a solvent and a polymer. At least one of the top cell plate and bottom cell plate comprises a plurality of lands, sealed source holes and/or unsealed source hole for penetration of a low-viscous fluid. Further, the method includes separating the top cell plate and the bottom cell plate to induce out of plane stretching of the high viscous fluid and obtaining a plurality of high aspect ratio structures between the top cell plate and the bottom cell plate due to the penetration of the low-viscous fluid.

14 Claims, 12 Drawing Sheets

METHOD AND APPARATUS FOR FABRICATING HIGH ASPECT RATIO STRUCTURES

FIELD OF INVENTION

The present disclosure relates to fabrication of structures, and more particularly to method and an apparatus for fabricating high aspect ratio structures. The present application is based on, and claims priority from International application numbered PCT/IN2020/050794 filed on 16 Sep. 2020 and Indian Application Number 202021034604 filed on 12 Aug. 2020, the disclosure of which is hereby incorporated by reference herein.

BACKGROUND

Generally, there is a high demand for High Aspect Ratio (HAR) multiscale structures for applications in areas like cell spheroid formation, tissue engineering, drug screening, biomedical engineering, medical devices, stem cell research and many more.

The existing methods of making multiscale structures uses material like polydimethylsiloxane (PDMS) and shape and size of the multiscale structures are controlled by changing the dimensions and position of mould pattern and by applying negative pressure. Also existing techniques for fabricating the multiscale structures include controlling Saffman-Taylor instability by providing pits over one of cell plates of a Lifted Hele-Shaw cell apparatus. Conventionally, shape of the multiscale structures is retained by curing of fluid used for fabricating the multiscale structures. The existing methods lack in providing plurality of controlled/uncontrolled HAR structures by controlling fluid instability in a Lifted Hele-Shaw cell.

Based on need for the applications, a controlled fabrication of high-aspect-ratio (HAR) 3D multiscale structures is required by effectively controlling Saffman-Taylor instability.

Thus, it is desired to address the above mentioned disadvantages or other shortcomings or at least provide a useful alternative.

OBJECT OF INVENTION

The principal object of the embodiments herein is to provide a method and an apparatus for fabricating high aspect ratio structures.

Another object of the embodiments herein is to effectively control Saffman-Taylor instability induced in a viscoelastic fluid for fabricating high aspect ratio structures, wherein the viscoelastic fluid is a blend of a solvent and a polymer.

Another object of the embodiments herein is to retain shape of high aspect ratio structures due to evaporation of the solvent of the viscoelastic fluid, wherein the solvent of the viscoelastic fluid is volatile.

Another object of the embodiments herein is to fabricate isolated high aspect ratio structure.

SUMMARY

Accordingly the embodiments herein disclose a method for fabricating high aspect ratio structures. The method includes depositing a predefined quantity of a viscoelastic fluid on a top surface of a bottom cell plate, wherein the viscoelastic fluid is a blend of a solvent and a polymer with or without additional particles. Further, the method includes compressing the viscoelastic fluid deposited on the top surface of the bottom cell plate using a bottom surface of a top cell plate, wherein at least one of the top cell plate and the bottom cell plate comprises the plurality of sealed source holes and/or the plurality of unsealed source holes for penetration of a low-viscous fluid. Further, the method includes separating the top cell plate and the bottom cell plate allowing out of plane stretching of the viscoelastic fluid while causing the penetration of surrounding low-viscous fluid. Further, the method includes obtaining a plurality of high aspect ratio structures between the top cell plate and the bottom cell plate due to the out of plane stretching of viscoelastic fluid, while undergoing rearrangement partly due to penetration of low viscous fluid.

In an embodiment, the high aspect ratio structure is a high aspect ratio 3D multi-scale structure.

In an embodiment, the top cell plate and the bottom cell plate is one of reactive to the solvent of the viscoelastic fluid and non-reacting to the solvent of the viscoelastic fluid.

In an embodiment, the viscoelastic fluid is deposited to form one of: a single fluid film and multiple isolated discontinuous fluid films on the top surface of the bottom cell plate when compressed using the bottom surface of the top cell plate.

In an embodiment, the top cell plate and the bottom cell plate are separated by retaining parallelism between the bottom cell plate and the top cell plate.

In an embodiment, the plurality of source hole comprise a plurality of land machined around the plurality of source hole to control a cross section of vertical walls of the high aspect ratio structures.

In an embodiment, obtaining the plurality of high aspect ratio structures between the top cell plate and the bottom cell plate due to the penetration of the low-viscous fluid includes forming of vertical walls of the high aspect ratio structures due to evaporation of the solvent of the viscoelastic fluid on the penetration of the low-viscous fluid, wherein the solvent of the viscoelastic fluid is volatile and obtaining the plurality of high aspect ratio structures between the top cell plate and the bottom cell plate.

Accordingly the embodiments herein disclose an apparatus for fabricating high aspect ratio structures. The apparatus includes the top cell plate and the bottom cell plate, wherein the plurality of high aspect ratio structures are obtained between the top cell plate and the bottom cell plate by depositing the predefined quantity of the viscoelastic fluid on the top surface of the bottom cell plate, wherein the viscoelastic fluid is the blend of the solvent and the polymer. Further, the embodiment includes compressing the viscoelastic fluid deposited on the top surface of the bottom cell plate using the bottom surface of the top cell plate, wherein at least one of the top cell plate and the bottom cell plate comprises the plurality of source hole for penetration of the low-viscous fluid. Further, the embodiment includes separating the top cell plate and the bottom cell plate to allow the penetration of the low-viscous fluid. Further, the embodiment includes obtaining the plurality of high aspect ratio structures between the top cell plate and the bottom cell plate due to the penetration of the low-viscous fluid.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

This invention is illustrated in the accompanying drawings, throughout which like reference letters indicate corresponding parts in the various figures. The embodiments herein will be better understood from the following description with reference to the drawings, in which.

DETAILED DESCRIPTION OF INVENTION

Figure 1:
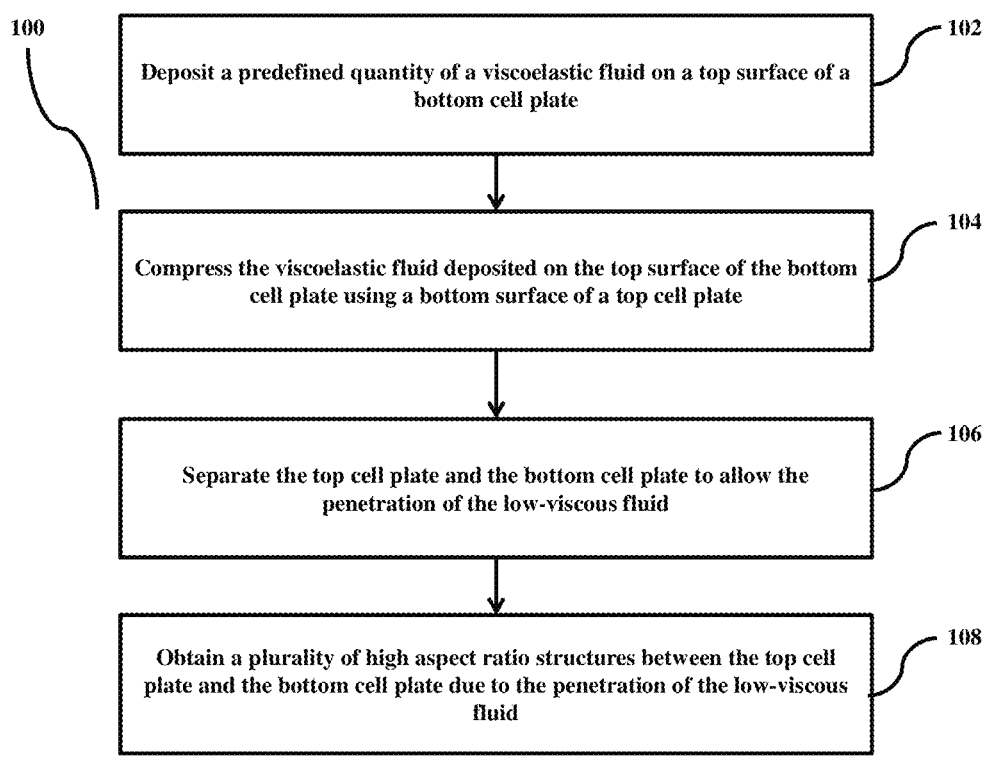
FIG. 1 is a flow diagram illustrating a method for fabricating high aspect ratio structures, according to an embodiment as disclosed herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. Also, the various embodiments described herein are not necessarily mutually exclusive, as some embodiments can be combined with one or more other embodiments to form new embodiments. The term "or" as used herein, refers to a non-exclusive or, unless otherwise indicated. The examples used herein are intended merely to facilitate an understanding of ways in which the embodiments herein can be practiced and to further enable those skilled in the art to practice the embodiments herein. Accordingly, the examples should not be construed as limiting the scope of the embodiments herein.

The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings. Although the terms first, second, etc. may be used herein to describe various elements, these elements should not be limited by these terms. These terms are generally only used to distinguish one element from another.

Accordingly the embodiments herein disclose a method for fabricating high aspect ratio structures. The method includes depositing a predefined quantity of a viscoelastic fluid on a top surface of a bottom cell plate, wherein the viscoelastic fluid is a blend of a solvent and a polymer. Further, the method includes compressing the viscoelastic fluid deposited on the top surface of the bottom cell plate using a bottom surface of a top cell plate, wherein at least one of the top cell plate and the bottom cell plate comprises a plurality of source hole for penetration of a low-viscous fluid. Further, the method includes separating the top cell plate and the bottom cell plate to allow the penetration of the low-viscous fluid. Further, the method includes obtaining a plurality of high aspect ratio structures between the top cell plate and the bottom cell plate due to the penetration of the low-viscous fluid.

Accordingly the embodiments herein disclose an apparatus for fabricating high aspect ratio structures. The apparatus includes the top cell plate and the bottom cell plate, where the plurality of high aspect ratio structures are obtained between the top cell plate and the bottom cell plate by depositing the predefined quantity of the viscoelastic fluid on the top surface of the bottom cell plate and the viscoelastic fluid is the blend of the solvent and the polymer. Further, the embodiment includes compressing the viscoelastic fluid deposited on the top surface of the bottom cell plate using the bottom surface of the top cell plate, where at least one of the top cell plate and the bottom cell plate comprises the plurality of sealed source holes and the plurality of unsealed source holes for penetration of the low-viscous fluid. Further, the embodiment includes separating the top cell plate and the bottom cell plate to allow the penetration of the low-viscous fluid. Further, the embodiment includes obtaining the plurality of high aspect ratio structures between the top cell plate and the bottom cell plate due to the penetration of the low-viscous fluid.

Referring now to the drawings and more particularly to FIGS. 1 through 12, where similar reference characters denote corresponding features consistently throughout the figure, these are shown preferred embodiments.

FIG. 1 is a flow diagram 100 illustrating a method for fabricating high aspect ratio structures, according to an embodiment as disclosed herein.

Referring to the FIG. 1, at step 102, a plurality of high aspect ratio structures is obtained between a top cell plate and a bottom cell plate of an apparatus by depositing a predefined quantity of a viscoelastic fluid on a top surface of the bottom cell plate. The viscoelastic fluid is a blend of a solvent and a polymer.

At step 104, the viscoelastic fluid deposited on the top surface of the bottom cell plate is compressed using a bottom surface of the top cell plate. The at least one of the top cell plate and the bottom cell plate includes a plurality of sealed source holes and a plurality of unsealed source hole for penetration of a low-viscous fluid. The low-viscous fluid can be air.

At step 106, the top cell plate and the bottom cell plate are separated to allow the penetration of the low-viscous fluid.

At step 108, the plurality of high aspect ratio structures is obtained between the top cell plate and the bottom cell plate due to the penetration of the low-viscous fluid.

The proposed embodiment describes a method for fabricating High-Aspect-Ratio (HAR) 3D multiscale structures by controlling fluid-fluid interface instability (Saffman-Taylor instability) induced in a fluid using the low viscous fluid. The fluid is the visco-elastic fluid and particularly a visco-elastic volatile polymer solution. The low viscous fluid possesses low viscosity in comparison to the visco-elastic fluid. An example for the low viscous fluid is air. The visco-elastic fluid is stretched into a thin fluid film in a Lifted Hele-Shaw Cell (LHSC) apparatus and random fluid-air interface destabilization and subsequent rearrangement of the visco-elastic fluid due to Saffman-Taylor instability is allowed. In the proposed embodiment, the HAR 3D multi-scale structures are fabricated or the fluid shaping is done by controlling the Saffman-Taylor instability.

The penetration of the low viscous fluid or air into the stretched fluid-film at multiple locations is controlled by pre-positioning tapered holes or the source-holes into one or both cell plates of the Lifted Hele-Shaw Cell (LHSC) apparatus. In the proposed embodiment, the penetration of air through the source holes rearranges the fluid into desired geometry of HAR 3D multiscale structures defined by shapes, sizes, orientations and positions of the source-holes. Again, the penetration of air into the stretched fluid at multiple locations is again controlled using the lands of various shapes machined around the source holes which control the cross-section of the stretched wall (vertical walls of the high aspect ratio structures). The proposed features of the embodiment such as the lands and the source holes is presented in several combinations of shapes, sizes, and need not be the same on both the cell plates. Further, dispensing of the visco-elastic fluid on the top surface of the bottom cell plate of the Lifted Hele-Shaw Cell (LHSC) apparatus is in a way that the visco-elastic fluid forms one of: single fluid film spanning all the features such as the lands or the source holes on the cell plates and multiple isolated discontinuous fluid films on the top surface of the bottom cell plate when compressed using the bottom surface of the top cell plate. The disclosure mentions about the High-Aspect-Ratio structures which also includes ultra-high Aspect-Ratio structures.

The various actions, acts, blocks, steps, or the like in the method may be performed in the order presented, in a different order or simultaneously. Further, in some embodiments, some of the actions, acts, blocks, steps, or the like may be omitted, added, modified, skipped, or the like without departing from the scope of the invention.

Figure 2A:
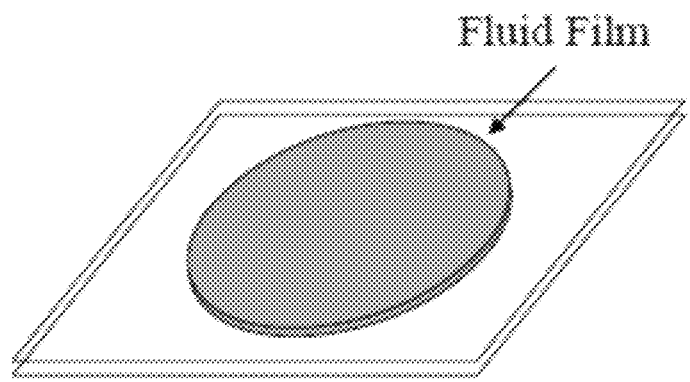
FIG. 2A is a schematic diagram illustrating a fluid film compressed between two cell plates of a Lifted Hele-Shaw Cell (LHSC) apparatus, according to a prior art.

FIG. 2A is a schematic diagram illustrating a fluid film compressed between two cell plates of a Lifted Hele-Shaw Cell (LHSC) apparatus, according to a prior art.

Figure 2B:
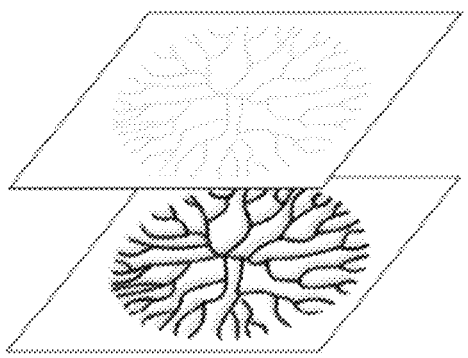
FIG. 2B is a schematic diagram illustrating a random (2D) fractal pattern formed due to a Saffman-Taylor instability in the LHSC apparatus, according to a prior art.

FIG. 2B is a schematic diagram illustrating a random (2D) fractal pattern formed due to a Saffman-Taylor instability in the LHSC apparatus, according to a prior art.

In existing methods and systems, by using the Saffman-Taylor instability (fluid-fluid interface instability), 2D fractal patterns is fabricated in the LHSC apparatus as illustrated in FIGS. 2A and 2B. The process of fabricating the 2D fractal patterns involves squeezing or compressing of a fluid between the two cell plates of the LHSC apparatus and then separation or lifting of the cell plates. The lifting of the cell plate induces a negative pressure-gradient in the stretched fluid film, dragging-in the surrounding air or the relatively low-viscous fluid to make-up for the extra space created. The displacement of the fluid film by the relatively low viscous fluid evokes the fluid-fluid interface instability known as the Saffman-Taylor instability. The Saffman-Taylor instability disintegrates the fluid-fluid interface at random multiple locations allowing the low-viscous fluid to penetrate as long fluid columns known as viscous fingers or penetrating fingers and the whole phenomenon is known as viscous fingering process. Uncontrolled or unequal positions or lengths of the penetrating fingers rearrange the fluid into a random branched network on both the cell plates as illustrated in FIG. 2B.

Figure 2C:
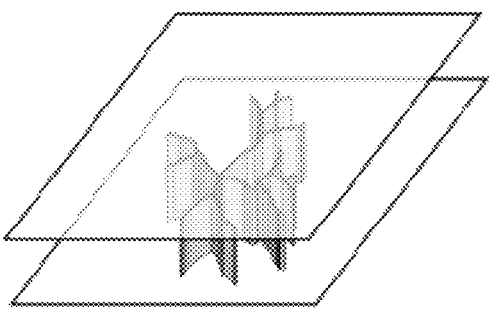
FIG. 2C is a schematic diagram illustrating a random high aspect ratio fractal pattern fabricated using the LHSC apparatus, according to an embodiment as disclosed herein.

FIG. 2C is a schematic diagram illustrating a random high aspect ratio fractal pattern fabricated using the LHSC apparatus, according to an embodiment as disclosed herein.

Referring to the FIG. 2C, the proposed method of fabricating high aspect-ratio (HAR) 3D multi-scale structures utilizes the Saffman-Taylor instability realized in a thin fluid film compressed and separated between two surfaces (the bottom surface and the top surface) of the cell plates (the bottom cell plate and the top cell plate) in the LHSC apparatus. The proposed method of fabricating the HAR 3D multi-scale structures utilizes the Saffman-Taylor instability which involves compressing of the viscoelastic fluid between two 'strategically modified' cell plates of the LHSC apparatus and is followed by a small delay, to let the relaxation of the normal stress, and then followed by separation or lifting of the cell plates. The lifting of the cell plate induces the negative pressure-gradient in the stretched fluid-film, dragging-in the surrounding air or the relatively low-viscous fluid to make-up for the extra space created. The Saffman-Taylor instability disintegrates the fluid-fluid interface at random multiple locations allowing the low-viscous fluid or air to penetrate as long fluid columns known as the viscous fingers or the penetrating fingers.

As seen in conventional methods and systems, uncontrolled or unequal positions or lengths of the penetrating fingers rearrange the fluid into the random branched network on both the cell plates. In the proposed embodiment, proper control of the Saffman-Taylor instability or the fluid-fluid interface instability results in the controlled method of fabricating high aspect ratio 3D multi-scale structures. Again, in the proposed embodiment the fluid used is the visco-elastic fluid and also the bottom cell plate and the top cell plate in the LHSC apparatus are modified to have anisotropies. With the visco-elastic fluid undergoing the controlled method of the Saffman-Taylor instability as illustrated in FIG. 2C, additional stretching of the viscoelastic fluid out-of-plane, while separating the bottom cell plate and the top cell plate of the LHSC apparatus results in the formation of thin vertical walls joining branched patterns created on the two cell plates as illustrated in FIG. 2C. The thin vertical walls joining the branched patterns created on the two cell plates are solidified upon evaporation of a volatile solvent in the viscoelastic fluid leaving behind solid 3D multi-scale structures.

Unlike existing systems, the resulting patterns or the 3D multi-scale structures possesses very High Aspect Ratio (HAR), for example 200-500 or more.

Unlike existing systems, the fluid used for fabricating the HAR 3D multi-scale structures is the viscoelastic fluid especially a viscoelastic polymer solution. The viscoelastic polymer solution is prepared by dissolving polymer in a volatile solvent. Due to the presence of the polymer in the solution, the fluid has viscoelasticity and due to evaporating solvent, the fluid has volatility. Thus, the fluid used in the proposed embodiment is a volatile polymer solution and due to viscoelasticity and volatility of the fluid high aspect ratio structure is fabricated.

In the proposed embodiment, the fluid shaping is done by controlling the Saffman-Taylor instability while separating the bottom cell plate and the top cell plate of the LHSC apparatus. Due to the viscoelasticity of the fluid, the fluid compressed between the bottom cell plate and the top cell plate is stretched to the 3rd dimension while separating the top cell plate and the bottom cell plate of the LHSC apparatus and shape of the HAR 3D multi-scale structures is retained due to evaporation of the volatile solvent that is evaporation of the volatile solvent from solution retains the shape of the HAR 3D multi-scale structures. 3D structure is formed due to viscoelastic and volatile nature of the fluid.

Unlike existing systems, the fabrication of the HAR 3D multi-scale structures using the proposed method is totally different and depends on surface tension, viscosity difference between displacing fluid (the viscoelastic fluid) and penetrating fluid or (the low viscous fluid—mostly air), the volatility of the fluid, and the concentration of the polymer in the solution or the fluid.

Figure 3A:
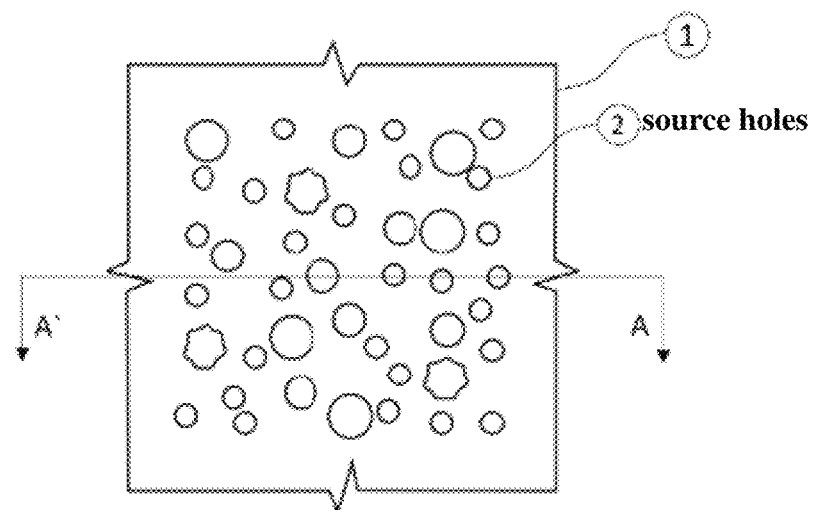
FIG. 3A is a schematic diagram illustrating a top sectional view of a Multiport Lifted Hele-Shaw Cell (MLHSC), according to an embodiment as disclosed herein.

FIG. 3A is a schematic diagram illustrating a top sectional view of the Multiport Lifted Hele-Shaw Cell (MLHSC), according to an embodiment as disclosed herein.

Figure 3B:
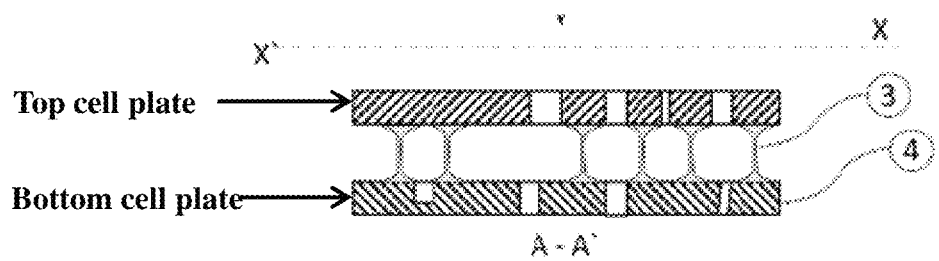
FIG. 3B is a schematic diagram illustrating a front sectional view of a Multiport Lifted Hele-Shaw Cell (MLHSC), according to an embodiment as disclosed herein.

FIG. 3B is a schematic diagram illustrating front sectional view of the Multiport Lifted Hele-Shaw Cell (MLHSC), according to an embodiment as disclosed herein.

Referring to the FIG. 3A and the FIG. 3B, in the proposed embodiment, the modified cell plates of the LHSC apparatus or the MLHSC apparatus includes pre-positioning or locating features like blind or sealed or open or tapered holes, termed as source holes, at different orientations and the source holes may be of uniform or non-uniform sizes and shapes. The various features of the MLHSC apparatus are shown in the FIG. 3A and the FIG. 3B. As shown in notation (1) of the FIG. 3A, the top cell plate may be of unrestricted shape and dimension. As shown in notation (2) of the FIG. 3A, the source holes may be of unrestricted shapes, sizes, and locations. As shown in notation (3) of the FIG. 3 B, out of plane fluid extension is guided by location and configuration of the source-holes. Notation (4) of the FIG. 3B represents a sectional view of the cell plates of the MLHSC apparatus containing the source holes of various configurations.

Figure 4A:
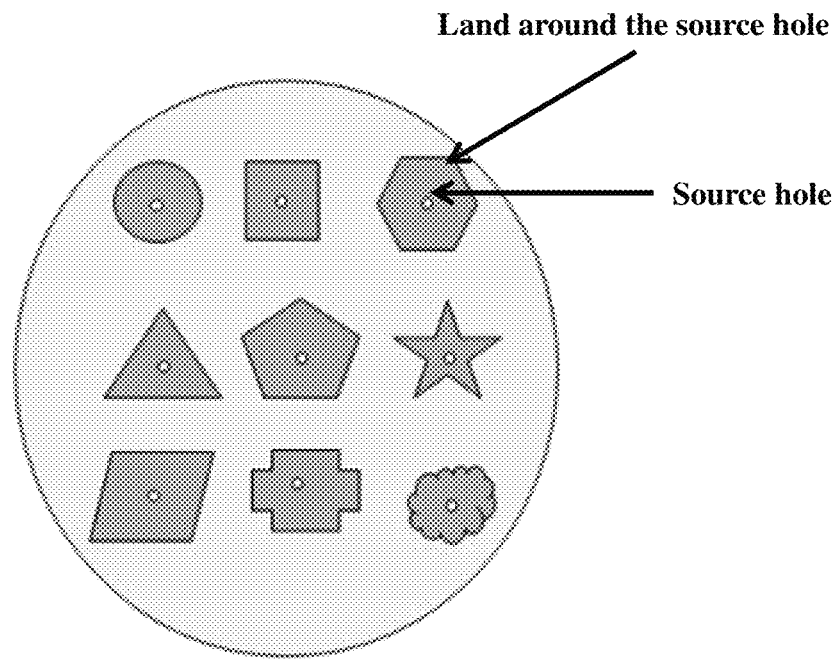
FIG. 4A is a schematic diagram illustrating a top view of a cell plate comprising different shapes of lands machined around source holes of the cell plate, according to an embodiment as disclosed herein.

FIG. 4A is a schematic diagram illustrating top view of a cell plate comprising different shapes of land machined around the source holes of the cell plate, according to an embodiment as disclosed herein.

Figure 4B:
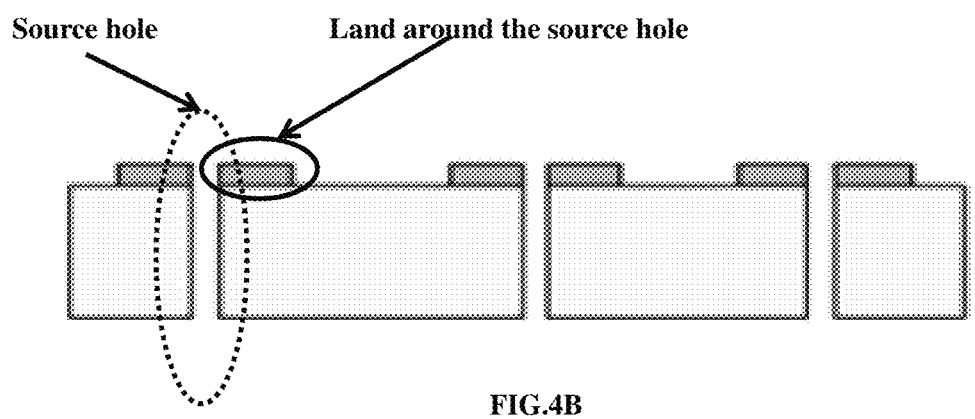
FIG. 4B is a schematic diagram illustrating side view of the cell plate comprising different shapes of lands machined around the source holes of the cell plate, according to an embodiment as disclosed herein.

FIG. 4B is a schematic diagram illustrating side view of the cell plate comprising different shapes of land machined around the source holes of the cell plate, according to an embodiment as disclosed herein.

Referring to the FIGS. 4A and 4B, different shapes of lands is machined on the cell plate around the source-hole. In the proposed embodiment, in addition to the source holes additional control of the Saffman-Taylor instability is introduced in the form of lands of various shapes machined or made around the source holes which controls a cross section of the stretched wall. As illustrated in the FIGS. 4A and 4B, a cross section of various shapes of the lands controls the cross section of the stretched wall. In the proposed embodiment, the features of the lands and the source holes may be present in several combinations of shapes, sizes, and need not be the same on both the cell plates.

The source holes act as a robust way to control the initiation of the viscous fingers while their shapes, sizes, orientation, and their relative unsealing would control the progression of fingers and finally affect the geometry of the HAR 3D multi-scale structures fabricated. Furthermore, in the proposed embodiment dispensing of the fluid is done in a way that either one single fluid film spanning all features (the lands and the source holes) on the cell plate is formed or multiple isolated fluid film islands when compressed is formed. In addition in the proposed embodiment, additional control of the Saffman-Taylor instability may be introduced using change of substrates of the bottom cell plate or the top cell plate used for the process: for example, glass, acrylic, metal, plastic, and so on: reactive or non-reacting to the solvent used in the viscoelastic fluid.

In the proposed embodiment, high aspect ratio structures may be fabricated by depositing the viscoelastic fluid to form a single fluid film of viscoelastic fluid on the top surface of the bottom cell plate and the single fluid film spanning an array of the source holes and without using the lands around the source holes.

In the proposed embodiment, high aspect ratio structures may be fabricated by depositing the viscoelastic fluid to form multiple isolated discontinuous fluid films on the top surface of the bottom cell plate with the array of source holes and without using the lands around the source holes.

In the proposed embodiment, high aspect ratio structures may be fabricated by depositing the viscoelastic fluid to form multiple isolated discontinuous fluid films on unit cell of an array of lands having a single source hole on each land or having multiple source holes on each land.

Figure 5A:
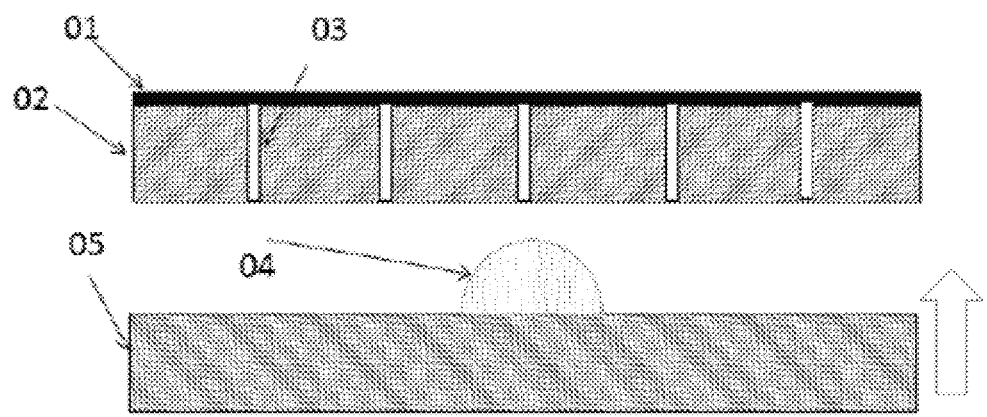
FIGS. 5A, 5B and 5C are schematic diagrams illustrating the Multi-Port Lifted Hele-Shaw Cell (MLHSC) operation for fabrication of high aspect ratio structures by depositing a viscoelastic fluid to form a single fluid film of the viscoelastic fluid on a top surface of a bottom cell plate, according to an embodiment as disclosed herein.
Figure 5B:
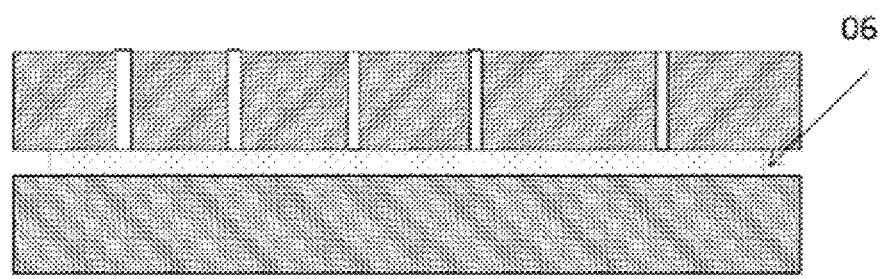
Figure 5C:
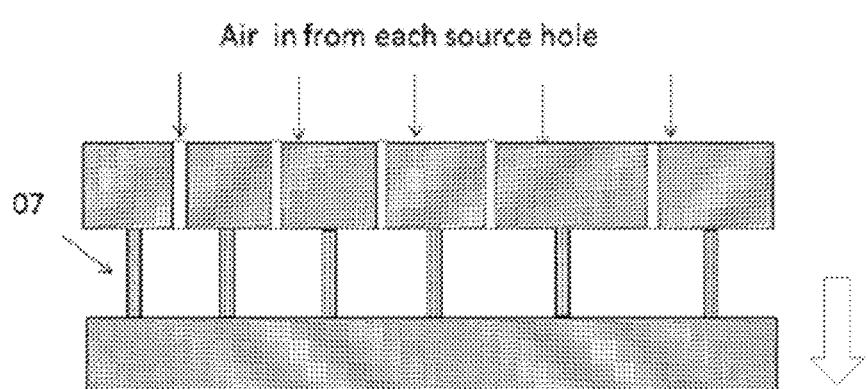

FIGS. 5A, 5B and 5C are schematic diagrams illustrating a Multi-Port Lifted Hele-Shaw Cell (MLHSC) operation for fabrication of high aspect ratio structures by depositing the viscoelastic fluid to form the single fluid film of viscoelastic fluid on the top surface of the bottom cell plate, according to an embodiment as disclosed herein.

Referring to the FIGS. 5A, 5B and 5C the high aspect ratio 3D multiscale structures may be fabricated by utilizing the single fluid film of the viscoelastic fluid deposited on the top surface of the bottom cell plate and the single fluid film is spanning the array of the source holes and without using the lands around the source holes.

In the proposed embodiment, the single fluid film is compressed and separated in between the cell plate having an array of holes, also termed as the multiport LHSC apparatus or the MLHSC apparatus. The final 3D multiscale structure fabricated post separation of the bottom cell plate and the top cell plate is high aspect ratio mesh of microwells where each microwell share walls with adjacent microwells. The schematic of the process of fabrication of the high aspect ratio of microwells is given in FIGS. 5A, 5B and 5C. Shape of the fabricated microwells are controlled robustly by placement of the source holes on the cell plates and the possible shapes are square, rectangle, hexagon, triangle, leaf venation, and so on.

FIGS. 5A, 5B and 5C illustrates the Multi-Port Lifted Hele-Shaw Cell (MLHSC) operation for fabrication of the high aspect ratio mesh of microwells with the volatile polymer solution and specifically with the visco-elastic volatile polymer solution. The notation (1) of the FIG. 5A represents seal. In the proposed embodiment, at least one of the top cell plate and the bottom cell plate includes pre-positioning or locating features like blind or sealed or open or tapered holes, termed as the source-holes, at different orientations and of uniform or non-uniform sizes and shapes. The notation (2) of the FIG. 5A represents the top cell plate, where the top cell plate is fixed. The notation (3) of the FIG. 5A represents the source hole. The notation (4) of the FIG. 5A represents a drop of visco-elastic volatile polymer solution deposited on the top surface of the bottom cell plate. The notation (5) of the FIG. 5A represents the bottom cell plate, wherein the bottom cell plate is movable.

The notation (6) of the FIG. 5B represents squeezed or compressed fluid film obtained on squeezing or compressing the drop of the viscoelastic fluid deposited on the top surface of the bottom cell plate using the bottom surface of the top cell plate. The notation (7) of the FIG. 5C represents a thin wall of a microwell fabricated on separating the top cell plate and the bottom cell plate.

Figure 6A:
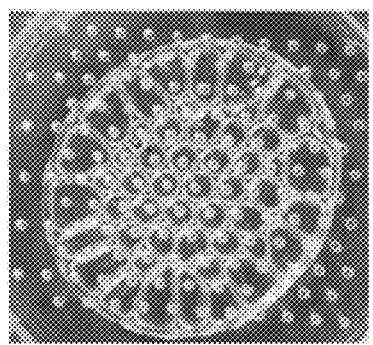
FIG. 6A and FIG. 6B are experimental images illustrating the high aspect ratio microwell-mesh structure of the viscoelastic volatile fluid, according to an embodiment as disclosed herein.
Figure 6B:
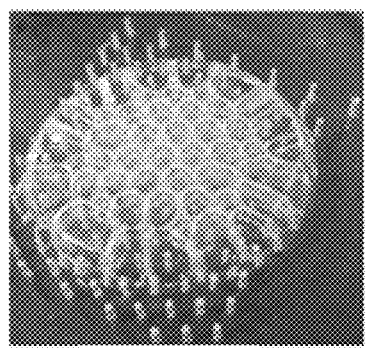
Figure 6C:
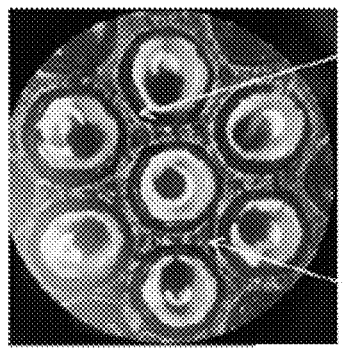
FIG. 6C illustrates a microscopic image of microwells, according to an embodiment as disclosed herein.
Figure 6C:
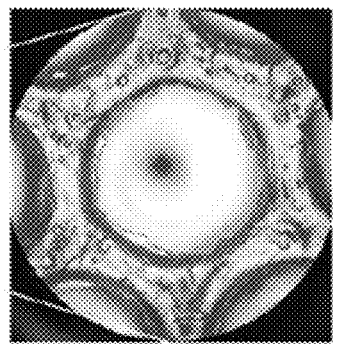

FIG. 6A and FIG. 6B are experimental images illustrating the high aspect ratio microwell-mesh structure of the viscoelastic volatile fluid, according to an embodiment as disclosed herein;

FIG. 6C illustrates a microscopic image of microwells, according to an embodiment as disclosed herein;

The high aspect ratio mesh of microwell structures is illustrated in the FIGS. 6A-6B where each microwell share walls with adjacent microwells.

Referring to the FIG. 6A, a top view of the high aspect ratio microwell-mesh structure is provided. The FIG. 6B is an oriented view of the high aspect ratio microwell-mesh structure. The FIG. 6C represents image of the top view of the high aspect ratio microwell-mesh structure under a microscope (Left) and magnified view of single hexagonal microwell (right).

Figure 7:
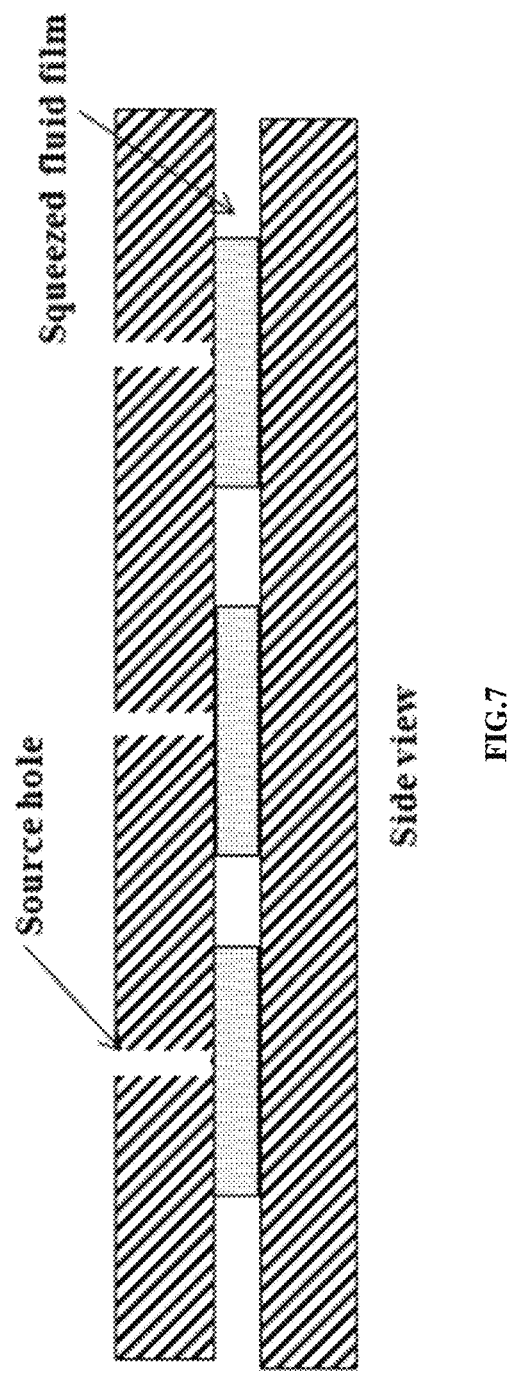
FIG. 7 is a schematic diagram illustrating multiple isolated discontinuous fluid films formed on the top surface of the bottom cell plate when compressed using a bottom surface of a top cell plate in the MLHSC apparatus, according to an embodiment as disclosed herein.

FIG. 7 is a schematic diagram illustrating multiple isolated discontinuous fluid films formed on the top surface of the bottom cell plate when compressed using the bottom surface of the top cell plate in the MLHSC apparatus, according to an embodiment as disclosed herein.

Figure 8:
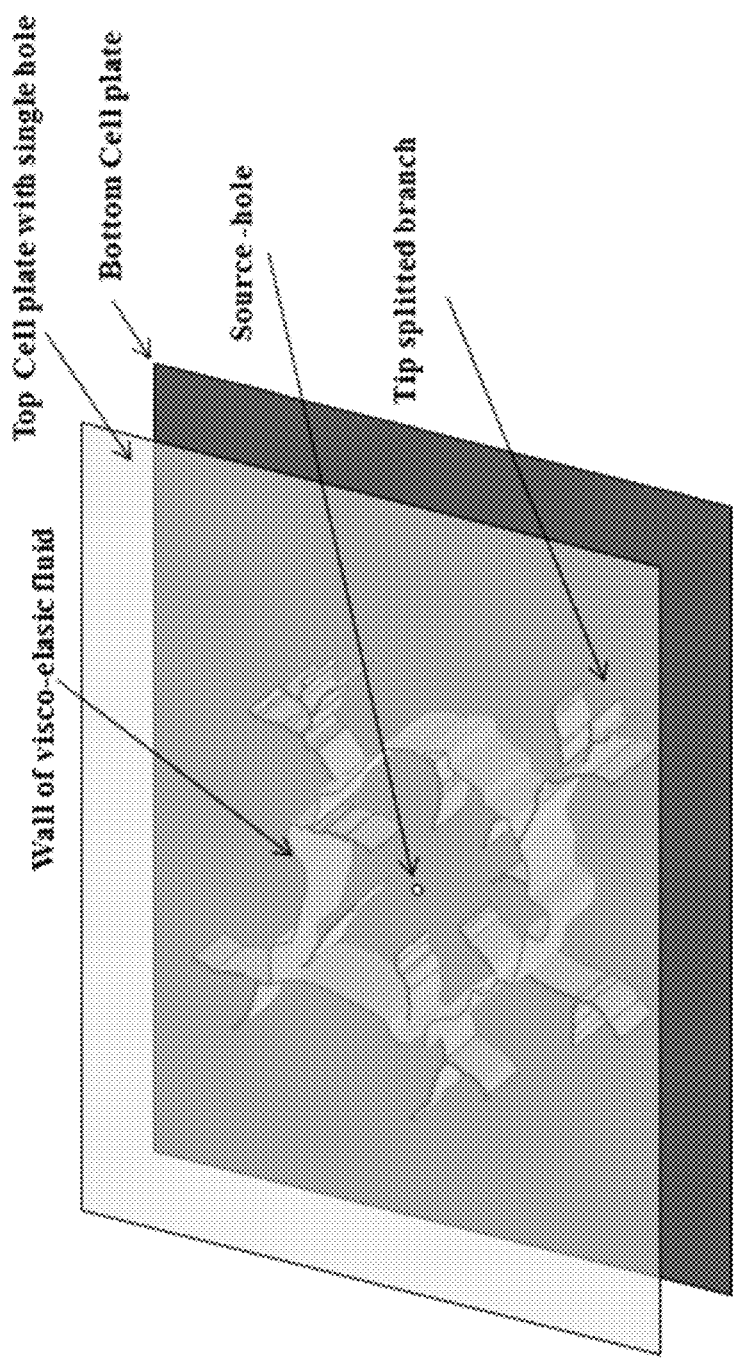
FIG. 8 is a schematic diagram illustrating a high aspect ratio microwell with branched boundary due to the Saffman-Taylor instability, according to an embodiment as disclosed herein.

FIG. 8 is a schematic diagram illustrating the high aspect ratio microwell with branched boundary due to Saffman-Taylor Instability, according to an embodiment as disclosed herein.

Figure 9:
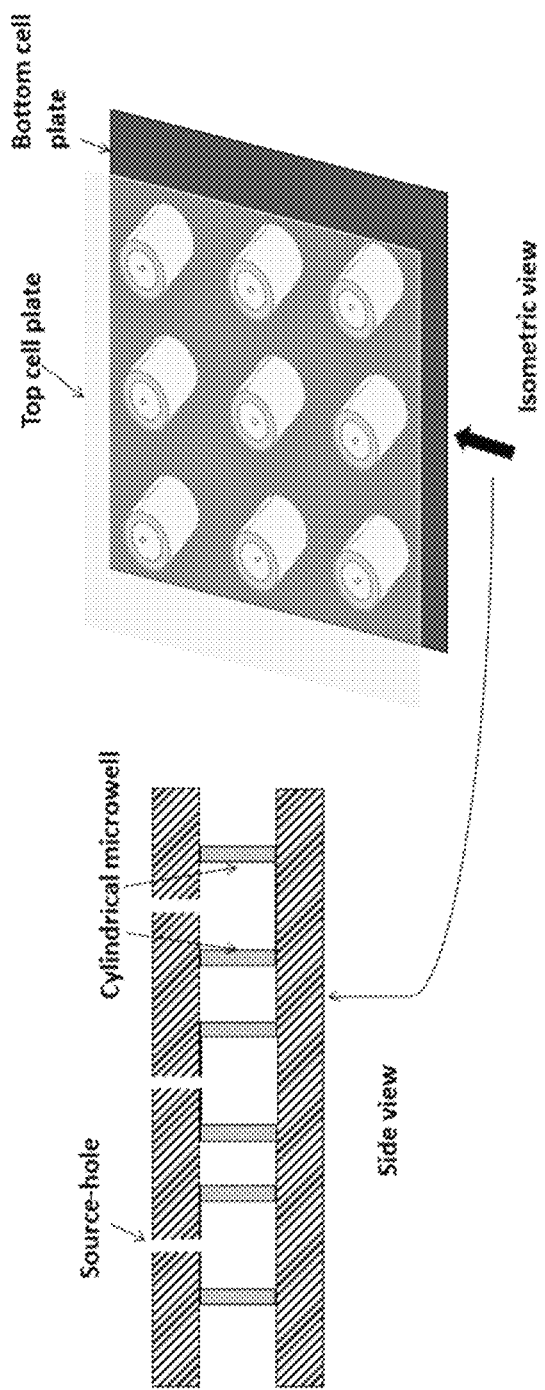
FIG. 9 is a schematic diagram illustrating an array of independent cylindrical microwell structures fabricated in the MLHSC apparatus with multiple isolated discontinuous fluid films, according to an embodiment as disclosed herein.

FIG. 9 is a schematic diagram illustrating an array of independent cylindrical microwell structure fabricated in the MLHSC apparatus with multiple isolated discontinuous fluid films, according to an embodiment as disclosed herein.

Figure 10:
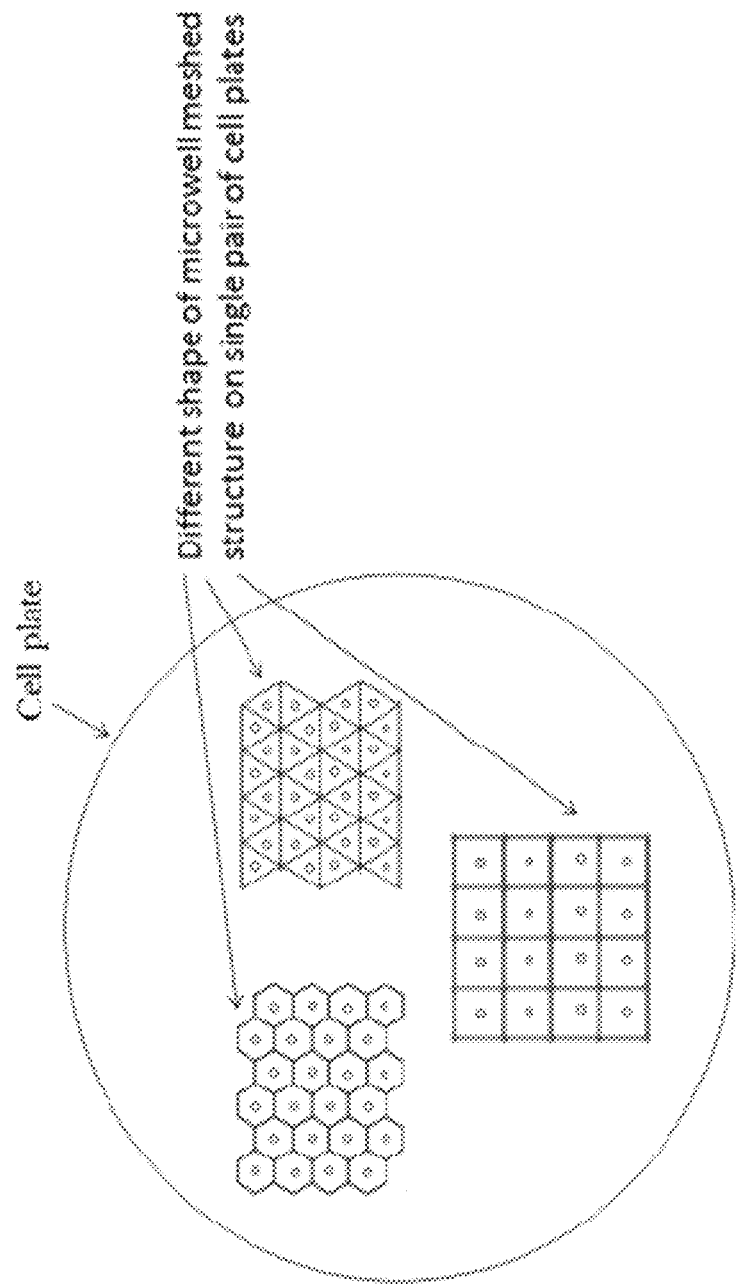
FIG. 10 is a schematic diagram illustrating various shapes of the microwell-mesh pattern on the MLHSC, according to an embodiment as disclosed herein.
Figure 11:
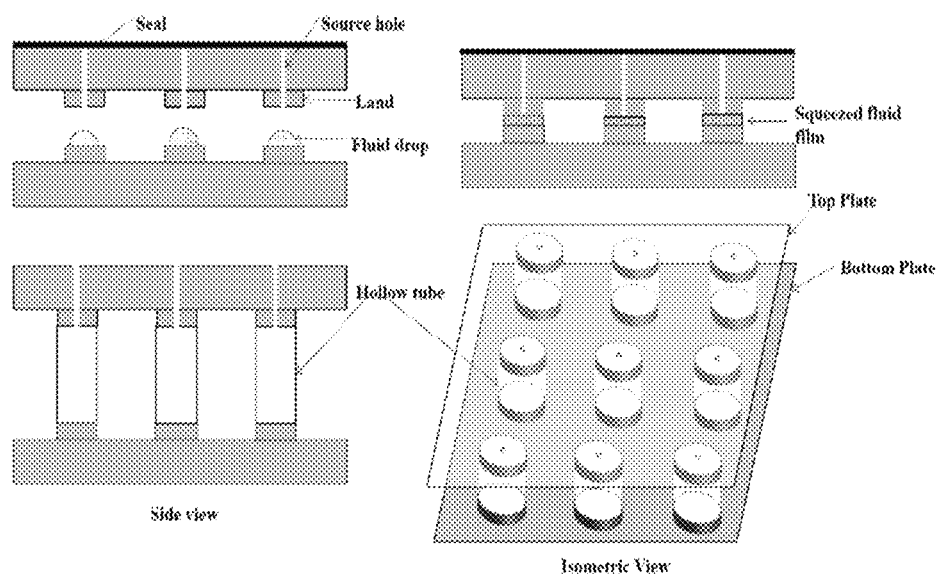
FIG. 11A is a schematic diagram illustrating fabrication of array of cylindrical microwell by using the land around source hole type anisotropy, according to an embodiment as disclosed herein.
FIG. 11B illustrates a single cylindrical microwell obtained during experimentation, according to an embodiment as disclosed herein.
Figure 11:
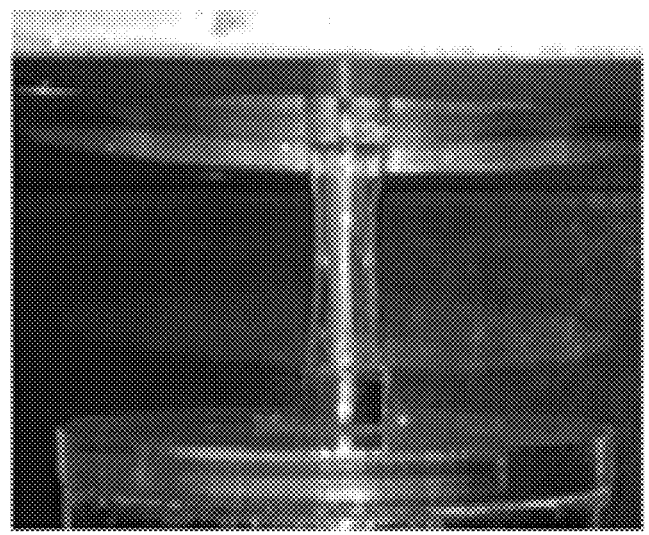

FIG. 10 is a schematic diagram illustrating various shapes of the microwell-mesh pattern on the MLHSC, according to an embodiment as disclosed herein.

Referring to the FIG. 7, the high aspect ratio 3D multiscale structures may be fabricated by utilizing the multiple isolated discontinuous fluid film islands of the viscoelastic fluid deposited on the top surface of the bottom cell plate and with the array of source holes and without using the lands around the source holes.

Instead of squeezing or compressing the single fluid drop between the top surface of the bottom cell plate using the bottom surface of the top cell plate in the MLHSC apparatus, multiple fluid drops are squeezed or compressed in between the cell plates in such a way that each fluid film does not touch adjacent fluid films and thus form isolated fluid film islands (as illustrated in FIG. 7). Since each fluid film does not touch adjacent fluid films, the microwells are evolved without their walls touching each other.

Upon separation of the cell plates, the final structure forms an array of micro or meso scale microwells pattern, where microwells are separated from each other. The boundary of the well may (as illustrated in FIG. 8) or may not be tip splitted (branch-like) depending on the experimental parameters for fabricating multiscale structures.

The proposed embodiment of fabricating the high aspect ratio structure by utilizing the multiple isolated discontinuous fluid film islands squeezed or compressed in the MLHSC with the array of source holes and without using the lands around the source holes results in various types of the high aspect ratio structures: (a) regular or irregular array structures where unit cell is just one independent well (as illustrated in FIG. 9, where there is no sharing of walls), or (b) where unit cell itself is array of wells (as illustrated in FIG. 10).

For example, the structure shown in FIG. 10 is fabricated if structure evolution from each fluid film island is controlled by different sets of array of source-holes on the same substrate of the cell plate. In this case, the shape of each mesh pattern depends on the arrangement of the source-holes. As shown in FIG. 10, it is possible to fabricate multiple sets of various shape microwell mesh structures on the single substrate of the cell plate.

In the proposed embodiment of fabricating high aspect ratio structure by utilizing multiple fluid isolated discontinuous film islands, there is limited control over shape and size of the outer most wall evolving out of the single squeezed island upon separation. For example, as illustrated in FIG. 9, the shape of well is always circular and the size is function of separation gap. Typically retraction of the outer fluid film boundary during lifting causes the lesser diameter of the microwell than the diameter of the initially squeezed fluid film. (FIGS. 8 and 9).

FIG. 11A is a schematic diagram illustrating fabrication of array of cylindrical microwell by using the land around source hole type anisotropy, according to an embodiment as disclosed herein.

Referring to the FIG. 11A, the high aspect ratio structure may be fabricated by utilizing multiple isolated discontinuous fluid film islands each on unit cell of the array of lands having single source hole on each land or having multiple source holes on each land.

In the proposed embodiment, anisotropy is introduced in the form of lands of various shapes machined around the source hole which controls the cross-section of the stretched wall of the fluid film or the cross section of vertical walls of the high aspect ratio structures on separating the top cell plate and the bottom cell plate.

In the proposed embodiment, the high aspect ratio (HAR) 3D multiscale structure is fabricated by squeezing a fluid drop on each pair of land. As the separation of top cell plate and bottom cell plate begins, two observations are noticed. The first observation is controlled or uncontrolled (due to Saffman-Taylor instability) evolution of air finger or the viscous finger from the source-holes. Another observation is the fastening or freezing of the outer fluid film interface to the edges of the land. The reason behind the fastening or freezing of the HAR 3D multiscale structure is the evaporation of the solvent from the stretching viscoelastic fluid guided by the lands on separating the top cell plate and the bottom cell plate. The viscoelastic fluid when comes in contact with the air causes evaporation of the solvent from the viscoelastic fluid and hence remaining fluid is fastened or freezed to the outer edge of the land. The viscous finger evolution from the source-holes and fastening or freezing of the outer fluid film interface to the edge of the land allows the collection of all the fluid along the land boundary. Fluid collected at the boundary of the land is stretched out of a plane on plate separation due to the viscoelasticity of the fluid. Also fastening or freezing of the fluid film boundary to the edges of the lands controls the cross-section of the stretched wall or the cross section of vertical walls of the high aspect ratio structures. Hence various sizes and shapes of the HAR microwell may be fabricated.

FIG. 11B illustrates a single cylindrical microwell obtained during experimentation, according to an embodiment as disclosed herein;

In the proposed embodiment, various type of structure like single microwell with various shape (as illustrated in the FIG. 11B), array of various shape independent microwell (as illustrated in FIG. 11A), array of various shape independent microwell mesh (as illustrated in FIG. 10, where each microwell mesh on different land) may be fabricated based on number of the lands and based on the source-hole pattern on each land. A real image of single cylindrical microwell is illustrated the FIG. 11B.

Figure 12A:
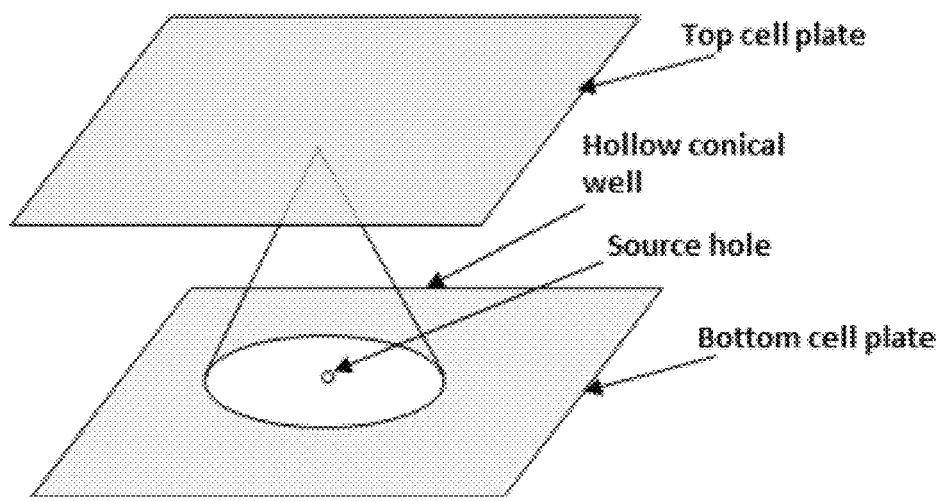
FIG. 12A is a schematic diagram illustrating a process of fabrication of a hollow conical microwell, according to an embodiment as disclosed herein.

FIG. 12A is a schematic diagram illustrating the process of fabrication of a hollow conical microwell, according to an embodiment as disclosed herein.

Figure 12B:
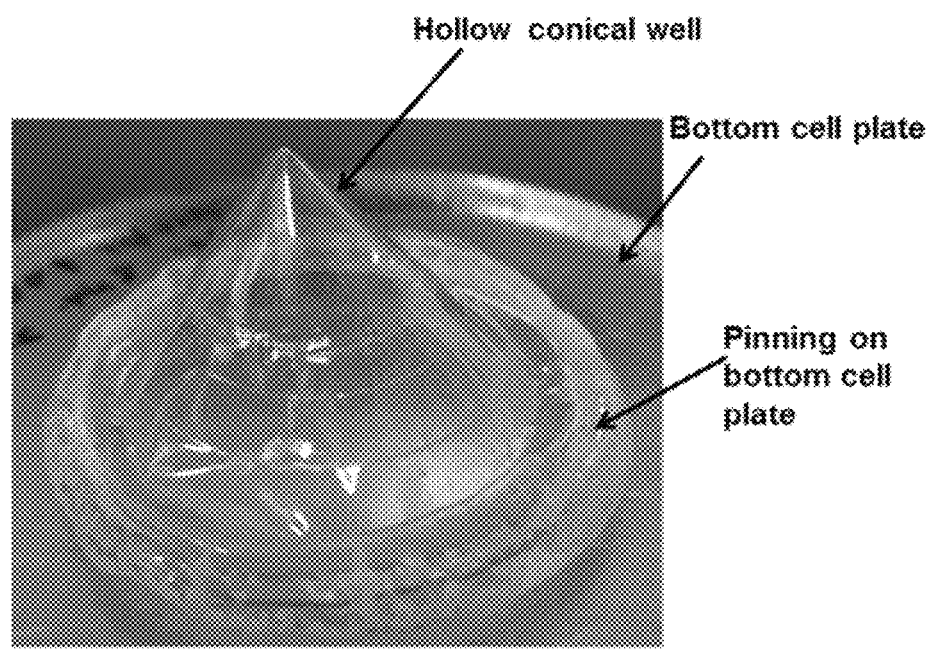
FIG. 12B is an example illustrating an image of the fabricated conical microwell, according to an embodiment as disclosed herein.

FIG. 12B is an example illustrating an image of fabricated conical microwell, according to an embodiment as disclosed herein.

Referring to the FIGS. 12A and 12B, the hollow conical microwell is fabricated using the proposed embodiment.

The main advantage of the proposed embodiment is a fabrication of the hollow conical microwell.

In the proposed embodiment of fabrication of the hollow conical microwell, for one of the cell plate, glass substrate is used and for the other cell plate acrylic substrate is used in the MLHSC apparatus. The solvent used in the viscoelastic fluid reacts chemically with the acrylic plate but not with the glass plate. The chemical reaction of the solvent in the viscoelastic fluid and the acrylic plate is utilized in forming the hollow conical microwell.

In the proposed embodiment, the fluid is squeezed between the acrylic plate and the glass plate. As shown in FIG. 12A, acrylic plate is having the source-hole. As the separation of the cell plates commence, pressure drop in the fluid film allows sucking air from the source holes. The air displaces the inner interface of the fluid film leaving the thin fluid film on both plates. The outer boundary of the fluid film does not retract due to the chemical reaction between the solvent in the fluid and the acrylic plate. Again further separation of the acrylic plate causes the release of the thin fluid film layer from the glass plate. The release of the thin fluid film layer starts from the outer boundary and step by step radially inward concentric fluid film layer gets released from the glass plate. At the time of releasing the thin fluid film layer from the glass plate simultaneous out of plane stretching of the fluid film is happened in such a way that the final structure takes conical shape (as illustrated in FIGS. 12A and 12B).

In the proposed embodiment, the viscoelasticity and the volatility are two important properties of the fluid for the fabrication of the HAR microwell. Out of plane stretching of the viscoelastic fluid is possible due to the viscoelasticity and retention of the HAR walls (fastening or freezing of the HAR walls) is possible due to the volatility of the fluid. Also, the viscoelasticity of the fluid varies by changing polymer concentration or the polymer molecular weight or the type of polymer and the volatility of fluid control by changing the concentration of solute or solvent. With the solvent, the solubility of the polymer also changes.

After controlled initiation of Saffman-Taylor instability, controlled progression or interaction of the low viscous fluid with the viscoelastic fluid is ensured by setting a plurality of cell parameter, mode of operation of the MLHSC and the fluid properties of the viscoelastic fluid such that all the viscous fingers grow stably. The plurality of cell parameter includes cell material, area of the fluid spread and thickness of the cell plate. The fluid properties include viscosity, surface tension, viscoelasticity and volatility of the viscoelastic fluid. The mode of operation of the LHSC or the MLHSC apparatus accounts for velocity of separation of the top cell plate and the bottom cell plate and its profile. Unstable growth of the viscous finger, which results in undesired, uncontrolled and complex phenomenon of fingertip-splitting may or may not be prevented by controlling the above-mentioned parameters based on the need for the application.

In the proposed embodiment, the transformation of the thin stretched fluid film into an arrangement with a large out-of plane extension is achieved by employing the viscoelastic fluid. Controlled progression of the viscous fingers, initiated from the source-holes, in XY plane is as a consequence of Saffman-Taylor instability while as out of plane stretching (in Z-direction) is guaranteed by a huge allowable strain of the viscoelastic fluid at higher and higher stretched conditions.

High aspect ratio 3D multiscale structure fabricated by the proposed method finds numerous applications in areas like cell spheroid formation, tissue engineering, drug screening, stem cell research and many more. With the degree of control achieved by the proposed method, high aspect-ratio structures with precise geometries and various layouts may be fabricated thus establishing the process as an alternate method of fabricating materials with smart properties called meta-materials.

With the proposed embodiment several types of the multiscale structures can be formed. The structure layout and feature dimensions of the HAR 3D multiscale structures are controlled by tuning the fluid rheology, the volatility of the fluid, the source-hole and the land layout, and the mode of the cell operation. This invention is an inexpensive and seam-less process of fabricating ultra-high aspect-ratio multiscale structures.

The proposed work is time efficient and cost effective as compared to other techniques available for fabrication of the high aspect ratio multiscale structure. The raw material for the fluid preparation is inexpensive and the proposed method is simple and fast. The possible applications are metamaterials for acoustics, well plates for chemical and biological assays including compound preparation, combinatorial chemistry, high throughput screening, and so on. Also other possibility, yet to be explored, is in the domain of energy.

The foregoing description of the specific embodiments will so fully reveal the general nature of the embodiments herein that others can, by applying current knowledge, readily modify and or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

We claim:

1. A method for fabricating high aspect ratio structures, the method comprising:
   depositing a predefined quantity of a viscoelastic fluid on a top surface of a bottom cell plate, wherein the viscoelastic fluid is a blend of a solvent and a polymer;
   compressing the viscoelastic fluid deposited on the top surface of the bottom cell plate using a bottom surface of a top cell plate, wherein at least one of the top cell plate and the bottom cell plate comprises a plurality of sealed source holes and a plurality of unsealed source holes for penetration of a low-viscous fluid, wherein the plurality of sealed source holes and the plurality of unsealed source holes comprise a plurality of land machined around the plurality of sealed source holes and the plurality of unsealed source holes to control a cross section of vertical walls of the high aspect ratio structures;
   separating the top cell plate and the bottom cell plate to allow the penetration of the low-viscous fluid; and
   obtaining a plurality of high aspect ratio structures between the top cell plate and the bottom cell plate due to out of plane stretching of the viscoelastic fluid while undergoing rearrangement due to the penetration of the low-viscous fluid.

2. The method as claimed in claim 1, wherein the high aspect ratio structure is a high aspect ratio 3D multi-scale structure.

3. The method as claimed in claim 1, wherein the top cell plate and the bottom cell plate is one of reactive to the solvent of the viscoelastic fluid and non-reacting to the solvent of the viscoelastic fluid.

4. The method as claimed in claim 1, wherein the viscoelastic fluid is deposited to form one of: a single fluid film and multiple isolated discontinuous fluid films on the top surface of the bottom cell plate when compressed using the bottom surface of the top cell plate.

5. The method as claimed in claim 1, wherein the top cell plate and the bottom cell plate are separated by retaining parallelism between the bottom cell plate and the top cell plate.

6. The method as claimed in claim 1, wherein obtaining the plurality of high aspect ratio structures between the top cell plate and the bottom cell plate due to the penetration of the low-viscous fluid comprises:
   forming of vertical walls of the high aspect ratio structures due to evaporation of the solvent of the viscoelastic fluid on the penetration of the low-viscous fluid, wherein the solvent of the viscoelastic fluid is volatile; and
   obtaining the plurality of high aspect ratio structures between the top cell plate and the bottom cell plate.

7. The method as claimed in claim 1, wherein the top plate and the bottom plate forms a lifted Hele-Shaw cell (LHSC).

8. An apparatus for fabrication of high aspect ratio structures, the apparatus comprising:
   a top cell plate; and
   a bottom cell plate, wherein a plurality of high aspect ratio structures are obtained between the top cell plate and the bottom cell plate by:
      depositing a predefined quantity of a viscoelastic fluid on a top surface of the bottom cell plate, wherein the viscoelastic fluid is a blend of a solvent and a polymer,
      compressing the viscoelastic fluid deposited on the top surface of the bottom cell plate using a bottom surface of the top cell plate, wherein at least one of the top cell plate and the bottom cell plate comprises a plurality of sealed source holes and a plurality of unsealed source holes for penetration of a low-viscous fluid, wherein the plurality of sealed source holes and the plurality of unsealed source holes comprise a plurality of land machined around the plurality of sealed source holes and the plurality of unsealed source holes to control a cross section of vertical walls of the high aspect ratio structures,
      separating the top cell plate and the bottom cell plate to allow the penetration of the low-viscous fluid, and
      obtaining the plurality of high aspect ratio structures between the top cell plate and the bottom cell plate due to the penetration of the low-viscous fluid.

9. The apparatus as claimed in claim 8, wherein the high aspect ratio structure is a high aspect ratio 3D multi-scale structure.

10. The apparatus as claimed in claim 8, wherein the top cell plate and the bottom cell plate is one of reactive to the solvent of the viscoelastic fluid and non-reacting to the solvent of the viscoelastic fluid.

11. The apparatus as claimed in claim 8, wherein the viscoelastic fluid is deposited to form one of: a single fluid film and multiple isolated discontinuous fluid films on the top surface of the bottom cell plate when compressed using the bottom surface of the top cell plate.

12. The apparatus as claimed in claim 8, wherein the top cell plate and the bottom cell plate are separated by retaining parallelism between the bottom cell plate and the top cell plate.

13. The apparatus as claimed in claim 8, wherein obtaining the plurality of high aspect ratio structures between the top cell plate and the bottom cell plate due to the penetration of the low-viscous fluid comprises:
   forming of vertical walls of the high aspect ratio structures due to evaporation of the solvent of the viscoelastic fluid on the penetration of the low-viscous fluid, wherein the solvent of the viscoelastic fluid is volatile; and obtaining the plurality of high aspect ratio structures between the top cell plate and the bottom cell plate.

14. The apparatus as claimed in claim 8, wherein the top plate and the bottom plate forms a lifted Hele-Shaw cell (LHSC).

* * * * *